(12) United States Patent
Sommer et al.

(10) Patent No.: US 6,192,280 B1
(45) Date of Patent: Feb. 20, 2001

(54) GUIDEWIRE PLACED IMPLANTABLE LEAD WITH TIP SEAL

(75) Inventors: John L. Sommer, Coon Rapids; Douglas S. Hine, White Bear Lake, both of MN (US)

(73) Assignee: Medtronic, Inc., Minneapolis, MN (US)

( * ) Notice: Under 35 U.S.C. 154(b), the term of this patent shall be extended for 0 days.

(21) Appl. No.: 09/324,460

(22) Filed: Jun. 2, 1999

(51) Int. Cl.$^7$ ........................................................ A61N 1/05
(52) U.S. Cl. ................................................................ 607/122
(58) Field of Search ................................. 607/122, 119, 607/120, 125; 600/373

(56) References Cited

U.S. PATENT DOCUMENTS

| | | |
|---|---|---|
| 3,769,984 | 11/1973 | Muench . |
| 4,355,646 | 10/1982 | Kallok et al. . |
| 5,003,990 | 4/1991 | Osypka . |
| 5,304,218 | 4/1994 | Alferness . |
| 5,381,790 | 1/1995 | Kanesaka . |
| 5,487,385 * | 1/1996 | Avitall ................................. 607/122 |
| 5,584,873 | 12/1996 | Shoberg et al. . |
| 5,755,765 | 5/1998 | Hyde et al. . |
| 5,755,766 | 5/1998 | Chastain et al. . |
| 5,800,495 | 9/1998 | Machek et al. . |

OTHER PUBLICATIONS

"Guidewire Placement of Electrical Lead" published as publication No. 35442 in Research Disclosure, Oct. 1993.

* cited by examiner

Primary Examiner—Scott M. Getzow
(74) Attorney, Agent, or Firm—Reed A. Duthler; Harold R. Patton; Girma Wolde-Michael

(57) ABSTRACT

A guidewire placed lead employing a seal at its distal end in order to prevent entry of body fluid into the lead. The seal is particularly designed to allow radial expansion of the outer circumference of the seal due to passage of the guidewire through the seal, reducing the force required to pass the guidewire through the seal, while retaining a good sealing characteristics. The seal may extend a distance distally from the tip electrode, and include a hollow, resilient, cup-shaped seal member, configured so that the seal can readily expand radially as the guidewire passes through it. Alternatively, the seal may be located within the body of the electrode and the electrode configured so that it may be radially or laterally expanded, also allowing radial expansion of the seal during passage of the guidewire. In this case, the electrode may be rendered expandable by means of one or more slits arranged along the electrode body, extending from a point proximal to the guidewire seal.

11 Claims, 4 Drawing Sheets

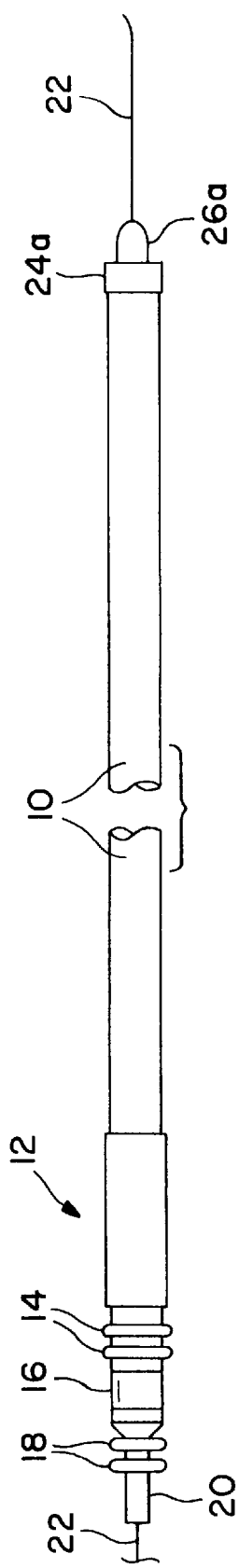
FIG. IA
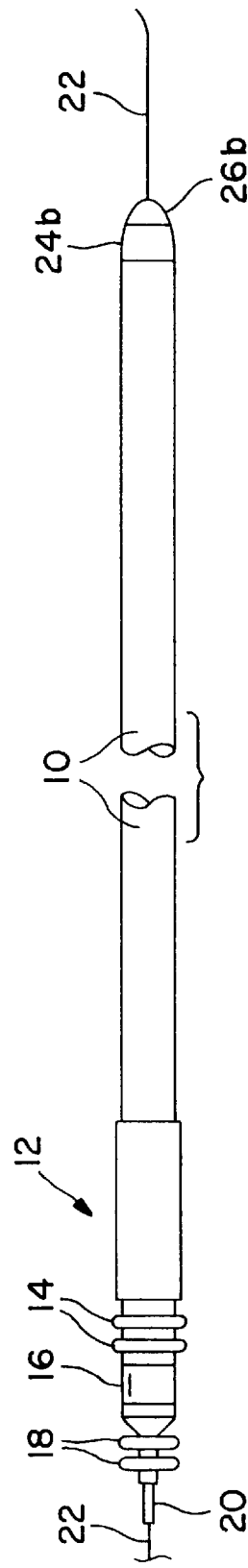
FIG. IB
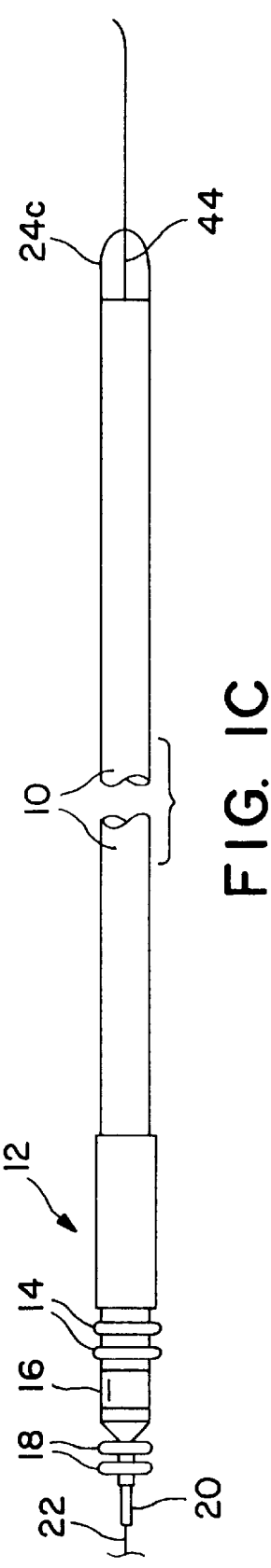
FIG. IC

GUIDEWIRE PLACED IMPLANTABLE LEAD WITH TIP SEAL

BACKGROUND OF THE INVENTION

The present invention relates generally to implantable medical leads, and more particularly to implantable leads placed by means of a guidewire.

Most commercially available cardiac pacing and defibrillation leads are placed by means of a stylet which is inserted into a central lumen through the lead, and is used to assist in pushing the lead through the vascular system and guiding it to a desired location. More recently, leads placed by means of a guidewire extending entirely through the lead and out its distal end have been introduced. Although such leads are new to commercial distribution, the basic idea of the guidewire placed lead goes back quite some time. One early example of a guidewire placed pacing lead is disclosed in U.S. Pat. No. 3,769,984 issued to Muench. In this lead, a central lumen extending through the lead and out its distal end is provided which may be used for pressure measurement or for use of a guidewire for guiding the lead during its insertion. In this lead, the guidewire lumen extends along the entire length of the lead body. Similar leads are disclosed in U.S. Pat. No. 5,755,766 issued to Chastain et al, and U.S. Pat. No. 5,800,495 issued to Machek et al.

In the context of coronary angioplasty catheters, the use of guidewires to place catheters within the vascular system has evolved to include the use of a "monorail" system, in which the guidewire lumen extends over only a distal portion of the catheter body. This basic approach has been adapted to cardiac pacing leads and cardioversion leads as well, as disclosed in U.S. Pat. No. 5,003,990 issued to Osypka, U.S. Pat. No. 5,755,765 issued to Hyde et al, U.S. Pat. No. 5,381,790 issued to Kenasaka and U.S. Pat. No. 5,304,218 issued to Alferness.

In guidewire implanted leads, there is a danger of blood entering the lumen of the lead body through the opening at the distal end of the lead through which the guidewire exits. It has been suggested in the anonymous publication "Guidewire Placement of Electrical Lead" published as publication no. 35442 in Research Disclosure, October 1993, that a pierceable silicone rubber membrane may be located at the distal tip of the lead, to prevent fluid entry into the lead body during and after placement of the lead.

SUMMARY OF THE INVENTION

The present invention is directed toward a guidewire placed lead employing a seal at its distal end in order to prevent entry of body fluid into the lead. Rather than being located inside a bore within the electrode or simply stretched across the distal tip of the electrode, the seal is particularly designed to allow radial or lateral expansion of the outer circumference of the seal due to passage of the guidewire through the seal. Such a design reduces the force required to pass the guidewire through the seal, while retaining a good sealing characteristics.

In two preferred embodiments of the invention, the seal extends a distance distally from the tip electrode, and includes a hollow, resilient, cup-shaped seal member, configured so that the seal can readily expand radially as the guidewire passes through it. The seal is preferably pre-pierced, to define a path through which the guidewire may pass. A third embodiment of the invention locates the seal within the body of the electrode, but configures the electrode so that it may be radially or laterally expanded, also allowing radial or lateral expansion of the seal during passage of the guidewire. In this case, the electrode may be rendered expandable by means of one or more slits arranged along the electrode body, extending from a point proximal to the guidewire seal. In this embodiment, the seal is also preferably pre-pierced to define a path through which the guidewire may pass.

BRIEF DESCRIPTION OF THE DRAWINGS

FIGS. 1a, 1b and 1c are plan views of the three described preferred embodiments of the invention.

FIG. 3 is a sectional view through the distal tip portion of the lead of FIG. 1a.

DETAILED DESCRIPTION OF THE PREFERRED EMBODIMENTS

Figure 2:
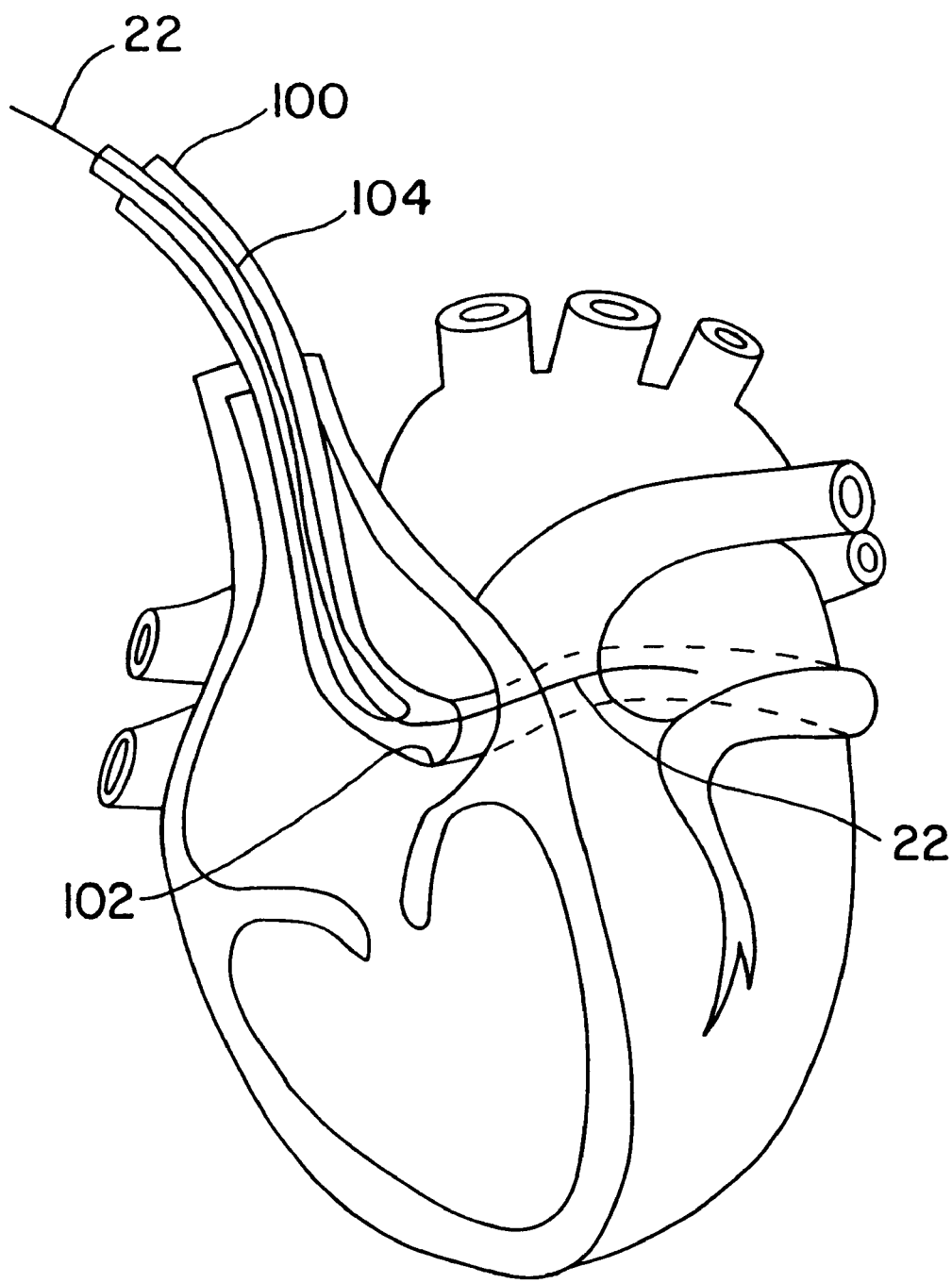
FIG. 2 is an illustration of the heart in conjunction with a schematic illustration of a lead according to the present invention in conjunction with an associated guidewire and guide catheter, illustrating placement of the lead in the coronary sinus of a human heart.

FIG. 1a illustrates a first embodiment of a lead according to the present invention. The lead is provided with an elongated insulative lead body 10 which in the embodiment illustrated takes the form of an insulative plastic or polymer tube, which carries a coiled conductor therein. Other lead body types may be substituted within the context of the present invention, including lead bodies employing multiple lumen tubes and/or stranded or braided conductors as disclosed in U.S. Pat. No. 5,584,873 issued to Shoberg et al, and incorporated herein by reference in its entirety. Alternatively, the lead may include additional conductors arranged either within a multi-lumen lead body or concentrically, as disclosed in U.S. Pat. No. 4,355,646 issued to Kallok et al and incorporated herein by reference in its entirety. Additional pacing electrodes, sensors, or defibrillation electrodes, may of course be added to the lead body and coupled to additional conductors.

At the proximal end of the lead body is a connector assembly 12 which takes the form of an IS-1 connector assembly conventionally used in commercially available cardiac pacing leads. The connector assembly includes a conductive connector pin 20 which is coupled by means of the conductor within lead body 10 to a tip electrode 24a located at the distal tip of the lead. A connector ring 16 is also provided which in the lead illustrated in FIG. 1a is not coupled to any electrode, but which in the context of leads employing additional electrodes would be coupled to a second conductor within lead body 10. Sealing rings 18 and 14 are provided to prevent fluid entry into the connector block into which the lead is inserted. A guidewire 22 is shown exiting the proximal end of the lead through connector pin 20 and exiting the distal end of the lead through seal member 26a. The configuration and operation of electrode 24a and seal member 26a are discussed in more detail in conjunction with FIG. 3, below. The use of a lead according to FIG. 1a is discussed in more detail in conjunction with FIG. 2, below.

FIG. 1b illustrates an alternative embodiment of the lead according to the present invention. All numbered elements correspond to identically numbered elements of the lead illustrated in FIG. 1a, with the exception that the configurations of the electrode 24b and seal member 26b are somewhat different. The configurations and function of electrode 24b and seal member 26b are discussed in more detail in conjunction with FIG. 4, below.

FIG. 1c is a plan view of a third embodiment of a lead according to the present invention. In this embodiment, the electrode 24c contains the seal member 26c (not visible in this view). It can also be seen in this view that the electrode 24c is provided with a longitudinal slot 44 which, as discussed below, allows for expansion of the electrode 24c during passage of the seal through the internal seal member 26c.

FIG. 2 is a schematic diagram of the lead 104 according to the present invention, which may correspond to any of the leads illustrated in FIGS. 1a, 1b and 1c or other embodiments of the present invention, passing through a guide catheter 100 and carrying a guidewire 22 extending through the entire length of the lead and out its distal end. As illustrated, the distal end 102 of guide catheter 100 is placed adjacent the opening of the coronary sinus and guidewire 22 extends into the coronary sinus. During implantation of the lead, the tip of guidewire 22 is advanced to a desired location within the patient's vascular system, for example the coronary sinus, and the lead 104 is passed along the guidewire 22 until it reaches its desired location. Use of a guide catheter 100 to facilitate advancement of the guidewire and/or the lead to a position adjacent its desired ultimate location, for example the ostium of the coronary sinus, is optional. After the lead is placed in its desired location, the guidewire 22 and the guide catheter 100 (if provided) are removed.

Figure 3:
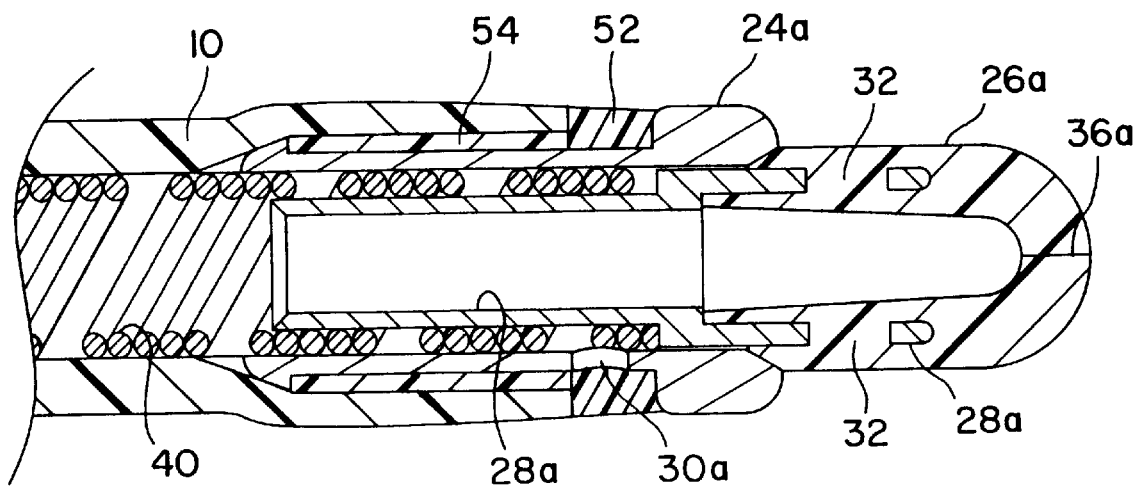

FIG. 3 is a sectional view through the distal portion of the lead of FIG. 1a. In this view it can be seen that the electrode 24a is coupled to a coiled conductor 40 by means of an internal conductive sleeve 28a. Electrode 24a may be crimped to compress conductor 40 between internal sleeve 28a and electrode 24a. Visual verification that conductor 40 is properly located prior to crimping is facilitated by bore 30a. The distal portion of inner sleeve 28a is provided with two bores 32, visible in this cross-section as filled with the material of the cup-shaped seal member 36a. By molding the cup-shaped seal member 36a to the distal portion of sleeve 28a, the bores 32 provide for a mechanical interlock of the seal and the sleeve. As illustrated at 36a, the cup-shaped seal member 26a is pre-pierced to define a path for the guidewire to pass through the seal.

The extension of the cup-shaped distal portion of seal 26a past the distal end of the sleeve 28a to which it is attached allows for radial expansion of the seal during passage of the guidewire. The seal 26a and electrode 24a are preferably configured so that the expanded diameter of the seal 26a during passage of the guidewire is still less than the outer diameter of the electrode 24a, so that the electrode 24a may still make contact with the heart, particularly in those circumstances in which the lead is employed as a coronary sinus lead. For example, in the embodiment illustrated, the diameter of seal member 36a in its relaxed position as illustrated is approximately 0.050 inches, and the diameter of electrode 24a is approximately 0.072 inches. With a 0.018 inch guidewire passed through seal 26a, the expanded diameter of seal 26a is approximately 0.068 inches, allowing electrode 24a to make contact laterally, for example with the wall of the coronary sinus, even while the guidewire is present. The proximal exposed edge of electrode 24a is radiused and extends slightly laterally outward (e.g. 0.002")

of insulative lead body 10, in order to further facilitate lateral contact of the electrode with body tissue, particularly in cases in which the lead is used in the patient's coronary sinus. The lead is optionally provided with a ring-shaped monolithic controlled release device 52, mounted around the electrode 24a. Controlled release device 52 preferably elutes an anti-inflammatory agent such as sodium dexamethasone phosphate, and may be fabricated as described in U.S. Pat. No. 4,972,848, issued to DiDomenico, et al., incorporated herein by reference in its entirety. A plastic band 54 is mounted around electrode 24a and lead body 10 is adhesively boned to the plastic band, coupling lead body 10 to the electrode.

Figure 4:
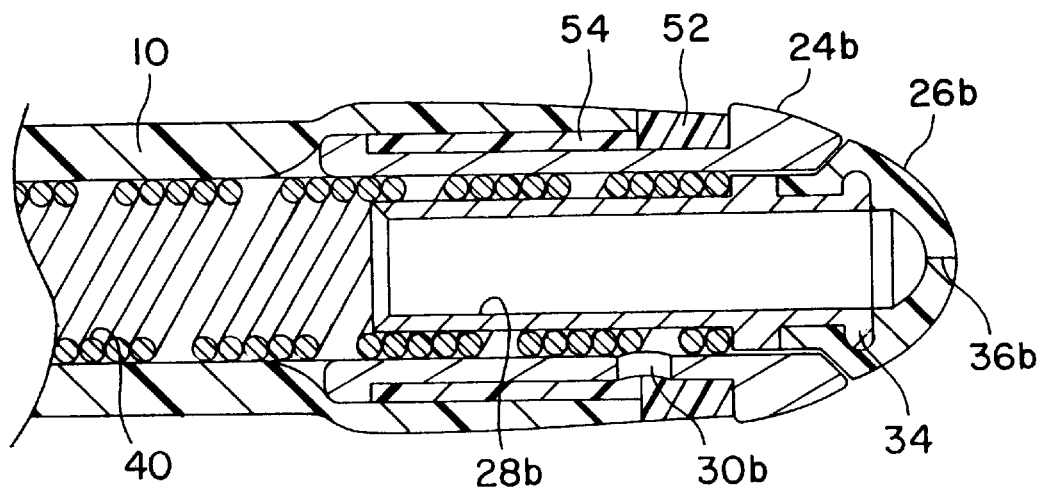
FIG. 4 is a sectional view through the distal tip portion of the lead of FIG. 1b.

FIG. 4 illustrates a sectional view through the distal portion of the lead illustrated in FIG. 1b. Identically labeled components correspond to those in FIG. 3. In this case, the electrode 24b is similarly provided with an internal conductive sleeve 28b, coupled to electrode 24b in the manner discussed in conjunction with FIG. 3. In this case, however, the sleeve 28b is provided with a laterally extending flange or ridge 34, and seal member 26b is retained by means of interaction of the laterally extending ridge 34 and the ring electrode 24b. In this case, the seal and electrode together are configured to provide a smooth rounded contour, without abrupt transitions, facilitating passage of the lead through the vascular system and in particular facilitating passage through the coronary sinus. As in the case of seal 26a, the distal tip of seal 26b takes the form of a cup-shaped member, allowing for radial expansion of the sleeve during passage of the guidewire through the sleeve. The sleeve is pre-pierced at 36b to define a path through which the guidewire passes,. As in the case of the seal 26a, one preferred material for fabrication of the seal is silicone rubber.

Figure 5:
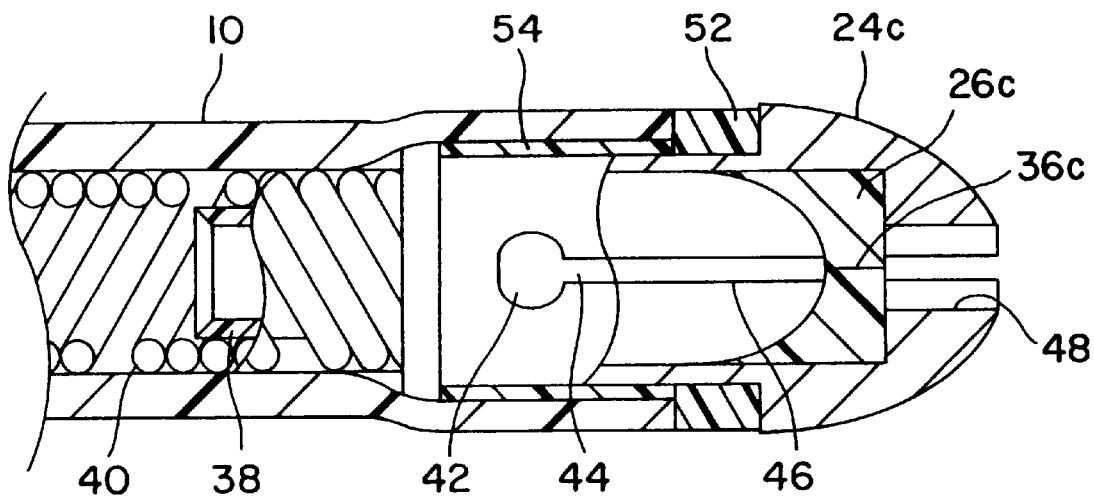
FIG. 5 is a sectional view through the distal tip portion of the lead of FIG. 1c.

FIG. 5 is a sectional view through the distal portion of the lead of FIG. 5. Identically numbered components correspond to those illustrated in FIGS. 3 and 4 above. In this embodiment, the seal 26c is located within the electrode 24c, rather than extending distally of it. While normally location of a seal within the electrode would prevent radial expansion of the seal during passage of the guidewire, electrode 24c is provided with two diametrically opposed longitudinal slots 44 and 46, allowing the distal ends of electrode 24c to spread apart from one another due to outward force exerted by seal 26c, during passage of a guidewire therethrough. The proximal ends of the slots 44 and 46 are optionally provided with enlarged circular recesses 44 to further facilitate the radial opening of the electrode 24c. The width of slots 44 and 46 is preferably less than the diameter of the guidewire, and is less than the diameter of the distal bore 48, which is slightly larger in diameter than the guidewire to be used with the lead. The configuration of slots 44 and 46 extends properly from the distal end of the electrode, during both advancement of the guidewire through the distal tip of the electrode and movement of the electrode along the guidewire during implantation of the lead. In the embodiment illustrated in FIG. 5, a crimping sleeve 38 is provided and coiled conductor 40 is crimped between sleeve 38 and electrode 24c in order to provide electrical connection thereto. As in the case of the leads illustrated in FIGS. 3 and 4, a preferred material for seal 26c is silicone rubber, and the seal is preferably pre-pierced at 36c as discussed above in conjunction with the leads of FIGS. 3 and 4.

Figure 6:
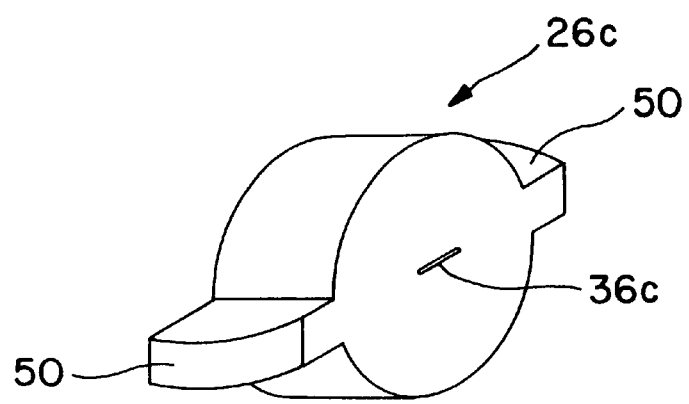
FIG. 6 is a perspective view of the seal member of the lead of FIGS. 1c and 5.

FIG. 6 illustrates seal member 26c in a perspective view. In this view, it can be seen that seal member 26c is provided with laterally extending ridges 50, which are configured to be located within slots 42 and 44, distal to lead body 10. Ridges 50 prevent fluid ingress into the electrode 24c along portions of the slots distal to the controlled release device 52, The ridges 50 may be adhesively bonded to the controlled release device 52 if necessary, to provide a reliable fluid seal.

In conjunction with the above, we claim:

1. An implantable lead, comprising:
    an elongated insulative lead body having a lumen extending through at least a distal portion of the lead body;
    an elongated conductor mounted within the lead body and extending along the lead body;
    an electrode mounted to a distal portion of the lead body, coupled to the conductor and having a lumen aligned with the lumen of the lead body and open to the distal end of the lead; and
    a generally cup-shaped resilient seal extending distally from the electrode.

2. A lead according to claim 1 wherein the electrode is further provided with an internal sleeve, mounted within the lumen through the electrode, and to which the cup-shaped seal is attached.

3. A lead according to claim 2 wherein said internal sleeve is provided with laterally directed bores and wherein the material of the resilient cup-shaped seal extends through the laterally extending bores to lock the seal to the sleeve.

4. A lead according to claim 2 wherein the internal sleeve is provided with a laterally extended ridge, engaging the cup-shaped resilient seal member.

5. An implantable medical lead, comprising:
    an elongated insulative lead body having a lumen extending through at least the distal portion of the lead body;
    an elongated conductor mounted within the lead body and extending along the lead body;
    an electrode mounted to a distal portion of the lead body and having a lumen therethrough aligned with the lumen of the lead body, and provided with means for allowing radial expansion of a portion of the electrode; and
    a resilient seal mounted within the lumen of the electrode, along the radial expandable portion of the electrode.

6. A lead according to claim 5 wherein the electrode is a tubular member and wherein the means for allowing expansion of the electrode comprises a slot extending longitudinally along the tubular member.

7. A lead according to claim 6 wherein the means for allowing radial expansion of the electrode comprises two horizontally opposed longitudinally extending slots.

8. An implantable medical lead, comprising:
    an elongated insulative lead body having a lumen extending through at least the distal portion of the lead body;
    an elongated conductor mounted within the lead body and extending along the lead body;
    an electrode mounted to a distal portion of the lead body and having a lumen therethrough aligned with the lumen of the lead body; and
    a resilient seal having a radially expandable portion through which a guidewire may pass and which displays an increased outer diameter during passage of a guidewire.

9. A lead according to claim 8 wherein the electrode is a tubular member and wherein the seal is mounted within the electrode and wherein the electrode is provided with slot extending longitudinally along the tubular member in the vicinity of the seal whereby the seal may expand radially during passage of a guidewire therethrough.

10. A lead according to claim 8 wherein the radially expandable portion of the seal is located distal to the electrode.

11. A lead according to claim 10 wherein the seal is a generally cup-shaped resilient seal extending distally from the electrode.

* * * * *